United States Patent [19]
Smith et al.

[11] Patent Number: 5,888,930
[45] Date of Patent: Mar. 30, 1999

[54] ASYMMETRIC MICROPOROUS BEADS FOR CONTROLLED RELEASE

[75] Inventors: Kelly L. Smith; Matthew F. Holmes, both of Bend; James W. Brooke, Sisters, all of Oreg.

[73] Assignee: Bend Research, Inc., Bend, Oreg.

[21] Appl. No.: 828,825

[22] Filed: Mar. 13, 1997

Related U.S. Application Data

[63] Continuation-in-part of Ser. No. 304,805, Jul. 12, 1994, abandoned, which is a continuation of Ser. No. 547,929, Jul. 2, 1990, abandoned, which is a continuation-in-part of Ser. No. 328,956, Mar. 27, 1989, abandoned.

[51] Int. Cl.$^6$ .............................. A01N 25/34; A61K 9/52
[52] U.S. Cl. ...................... 504/116; 71/64.1; 71/DIG. 1; 424/419; 424/501; 424/502; 424/409; 514/963; 514/964
[58] Field of Search ...................................... 514/963, 964; 424/419, 501, 502, 409; 504/116; 71/64.11, DIG. 1

[56] References Cited

U.S. PATENT DOCUMENTS

| 4,191,812 | 3/1980 | Chong | 521/28 |
|---|---|---|---|
| 4,515,906 | 5/1985 | Friesen et al. | 521/28 |
| 4,670,250 | 6/1987 | Baker | 424/419 |
| 4,690,825 | 9/1987 | Won | 424/501 |

*Primary Examiner*—S. Mark Clardy
*Attorney, Agent, or Firm*—Chernoff, Vilhauer, McClung & Stenzel, LLP

[57] ABSTRACT

A durable and sprayable controlled release bead of active ingredient in the pores of a polymeric micro-porous bead having an anisotropic pore structure of large pores in the interior and small pores at the surface, the gradation of pore sizes between the interior and the surface being continuous.

12 Claims, 4 Drawing Sheets

ASYMMETRIC MICROPOROUS BEADS FOR CONTROLLED RELEASE

This is a continuation-in-part of application Ser. No. 08/304,805 filed Sep. 12, 1994, now abandoned, which is a continuation of application Ser. No. 07/547,929 filed Jul. 2, 1990, now abandoned, which is a continuation-in-part of application Ser. No. 07/328,956 filed Mar. 27, 1989, now abandoned.

BACKGROUND OF THE INVENTION

Controlling the release of such active ingredients as pharmaceuticals, fragrances, insecticides, and other agricultural chemicals has proven to be extremely useful for providing valuable advantages over conventional products. Such advantages include longer durations of efficacy, decreased toxicity, and more flexibility and convenience in handling and application. Control of the release of active ingredients has been achieved by diffusion through membranes, diffusion through pores, osmotic pumping, erodible polymers, mechanical fracture, electrical energy, and other means appropriate for specific applications.

For applications in which it is desirable or necessary for the active ingredient to be sprayed or distributed in particulate or liquid-suspension form, controlled-release microcapsules, granules, and porous particles have been developed. Many different types of microencapsulation processes have been developed, as described for example in Nixon, "Microencapsulation" (1976). Microencapsulation, however, involves polymerizing or solidifying a polymeric shell around a core of the active ingredient, and the active ingredient is therefore present during the entire process. Although this is not a problem with many active ingredients, some are degraded or otherwise affected by the processing conditions, and not all of the active ingredient is microencapsulated, due to solubility in the liquid phases present or to inefficiency in the process itself. Due to interactions between the active ingredient and the polymer, solvent, or other chemicals, the range of active ingredients, as well as polymer, is limited. In addition, solvents, reactants, or other ingredients used in microencapsulation processes may remain in the microcapsules with the active ingredient, which may cause toxicity or further degradation problems. Washing the microcapsules to remove contaminants is usually not practical, because some of the active ingredient will be lost as well. Additional problems with microcapsules include a limitation on size (usually to smaller than about 200 microns in diameter), a limitation on strength, and a limitation on content of active ingredient, especially in combination with high strength.

Porous granules or particles to provide controlled release are also known. Such porous particles can be made in the absence of active ingredient, thus eliminating problems related to interactions between the active ingredient and particle materials, and enabling the particles to be extracted or cleaned, if necessary, prior to loading with active ingredient. However, unless the pore sizes are small, the active ingredient is typically released too rapidly to be useful. In addition, it is typically released by desorption, evaporation, or by leaching, all of which are dependent on the environment of use. For example, in U.S. Pat. No. 4,111,684, there are disclosed porous cellulosic particles subsequently loaded with herbicides that must be water-leachable.

Other examples of microporous cellulosic particles are disclosed in U.S. Pat. Nos. 3,985,298 and 3,846,404. These particles shrink upon drying, and must therefore be loaded by a complicated process of diffusive exchange of the water initially present with the active ingredient desired, taking care to avoid drying. In a further example of microporous particles of controlled release, U.S. Pat. No. 3,639,306 discloses the preparation of active ingredient-encapsulating particles having a finely porous skin on the surface and a substantially hollow interior containing the active ingredient. Although such active ingredient-encapsulating particles are stated to be useful for slow release of active ingredient, due to depletion of active ingredient in the reservoir over time and the consequent decrease in active ingredient-releasing surface area, the rate of release of active ingredient decreases with time, rather than being constant.

In summary, there is a need in the art for high strength sprayable granules or particles that can be prepared independently of loading with active ingredient, and that can release active ingredient at a constant rate over a prolonged period of time.

SUMMARY OF THE INVENTION

According to the present invention, asymmetric microporous beads are provided that can be prepared prior to loading them with active ingredient, that can contain up to 90% active ingredient, that are exceptionally durable and sprayable, and that can release essentially all of the active ingredient at a constant rate over long periods of time. These advantages are realized in part due to the asymmetric structure of the microporous beads, the asymmetry comprising a continuous gradation of pore sizes from very small pores near the surface to very large pores in the interior of the bead.

DETAILED DESCRIPTION OF THE INVENTION

Figure 1:
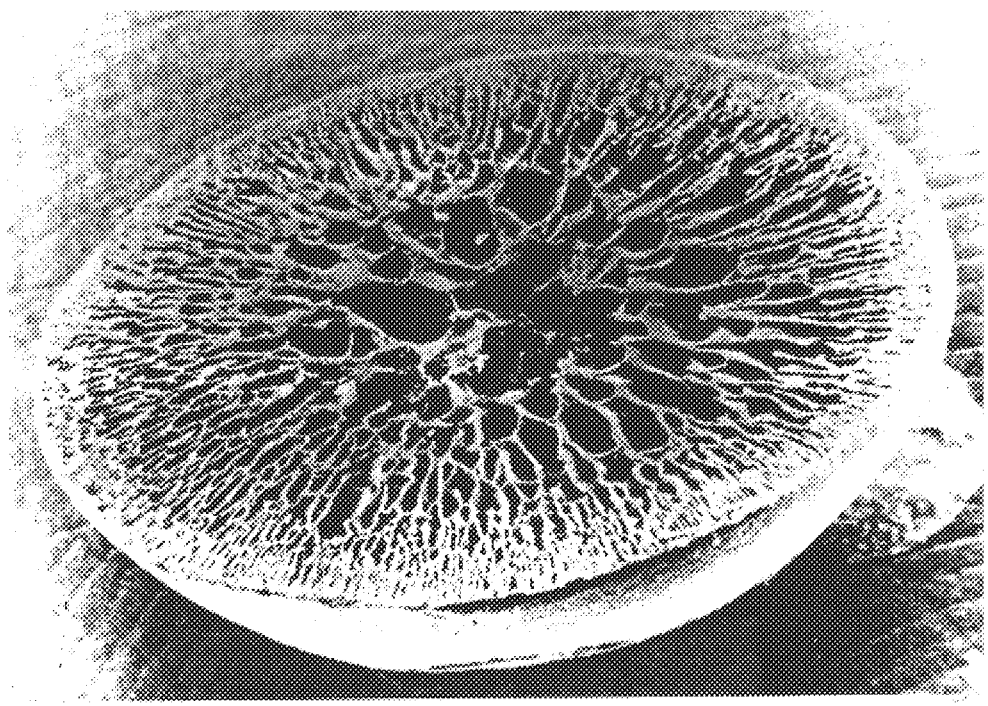
FIG. 1 shows a scanning electron photomicrograph of a cross-section of a bead of the present invention.

The beads of the present invention are made of film-forming polymers, they have a generally spherical shape with diameters ranging from about 5 microns to about 5 mm, and they have a unique, continuously-gradated asymmetric microporous structure, with small pores near the surface and progressively larger pores toward the interior core. They are typically loaded with active ingredient following preparation of the beads, and the active ingredient is released at a slow and substantially constant rate over an extended period of time.

Polymers useful for preparation of the beads of the present invention include polycarbonates, polysulfones, polyamides, polyurethanes, acrylic resins, polyvinyl chloride, polyvinyl fluoride, polyacrylonitrile, polystyrene, polyolefins, polyvinylidene chloride, polyvinylidene fluoride, polyethyleneterephthalate, polybutyleneterephthalate, cellulose acetate and other cellulosic esters, polyimides, polyacetals, polyvinylacetate, polyphenyleneoxide, polyetherimides, ethylenevinyl-alcohols, and derivatives and copolymers of the above. Useful polymers must be soluble in a suitable solvent and insoluble in a liquid that is miscible with the solvent. Typical polymer concentrations in the polymer solution are from 50 to 300 g/L. Solvents useful in the present invention must dissolve the polymer and be miscible with the liquid, typically water, used for precipitation.

The key to achieving the characteristic continuously-gradated asymmetric pore structure of the beads of the present invention is keeping the rate of solvent exchange with the liquid of the precipitation bath slow following a rapid initial precipitation that forms the "skin" layer. Typically, such solvent exchange takes more than an hour to complete, depending on the size of the beads. In order to retard the rate of solvent exchange, solvent may be added to the precipitation bath in an amount that still allows the beads to initially precipitate rapidly in the bath; suitable amounts range from 5 to 20 wt %.

Another method of retarding the rate of solvent exchange sufficiently to permit the continuously-gradated pore structure is to use high-viscosity polymer solutions which slow the rates of diffusion of both the solvent out of the bead and the precipitation bath liquid into the bead. Suitable viscosities, depending upon the polymer, solvent, and precipitation bath used, vary from about 500 to about 2000 cps; generally it may be said that the viscosity of the polymer solution must be $\geq 500$ cps to achieve the continuously-gradated asymmetric pore structure of the beads of the present invention. In fact, such high-viscosity solutions can enable beads with the desired asymmetric structure to be formed without the use of solvents in the precipitation bath, which simplifies manufacture and solvent recovery.

A third method of achieving the initial rapid "skin"-forming precipitation, followed by the slower rate of solvent exchange (or precipitation), is to heat the polymer solution to lower its viscosity to the proper range which simultaneously permits the solution to dissolve more polymer to the point of supersaturation. Both the temperature differential and the supersaturated concentration of polymer contribute to a more rapid rate of precipitation at the finely porous skin layer of the forming bead when the droplet of polymer solution is dispersed in the precipitation bath. The formation of the finely porous skin layer tends to create a barrier between the bath and the interior of the bead, the barrier becoming thicker over time, thus slowing down the rate of heat and mass transfer between the polymer/solvent droplet and the bath; this in turn gradually slows the rate of precipitation at the interior of the bead, with the center of the bead precipitating the most slowly.

In order to achieve the continuously-gradated pore structure of the beads of the present invention, the polymer, its solvent, and the precipitation bath must all be specified. Examples of polymer/solvent bath combinations that result in asymmetric microporous beads of the invention include: polysulfone/dimethylformamide/water, polyvinylidenefluoride/dimethylformamide/water-dimethylformamide; polyvinylchloride/dimethylformamide/water dimethylformamide; polyurethane/dimethylformamide/water; and cellulose acetate/dichloromethane-dimethylformamide/water.

The beads of the present invention are prepared by first dissolving the polymer in a solvent or solvent mixture, then spraying droplets of the solution thus formed into a stirred precipitation bath containing a liquid, typically water, that is miscible with the solvent, allowing the precipitated beads to remain in the bath until substantially all of the solvent has been removed or exchanged, and then collecting the beads and drying them, if desired.

The beads can then be loaded with an active ingredient or mixture of ingredients in either liquid or solid form. Loading with liquid active ingredient is accomplished by submerging dry beads in the liquid, and either drawing a vacuum on the solution or pressurizing the solution to force the liquid into the interior continuously-gradated porous structure of the beads. This process of loading the beads with active ingredient following preparation of the beads avoids contact of the active ingredient with the solvent or with the precipitating liquid, a typical prior art procedure, which greatly reduces loss of the active ingredient into those liquids. Alternatively, if the active ingredient is substantially insoluble in the precipitating liquid, the active ingredient can be added to the polymer solution before spraying into the precipitating bath. This alternative method of loading is most useful for solid active ingredients with low solubilities in the solvent and precipitating liquid. Loading methods are explained in greater detail below.

The polymer solution must have a sufficiently low viscosity to enable spraying or dripping the solution out of a nozzle. This is generally a viscosity lower than about 4000 cps, and preferably lower than about 2000 cps. At the same time, as previously mentioned, it must also have a sufficiently high viscosity to retard the rate of solvent exchange so as to permit the pores to be continuously gradated from small pores at the surface to large pores in the interior. The range of viscosities meeting both of these requirements is about 500–2000 cps. Viscosities lower than 500 cps usually result in undesired substantially hollow bead interiors, wherein the transition between the micropores at the surface and the macropores in the interior is sudden rather than continuous, taking place within a micron or less of geometric space. High viscosity polymer solutions enable the asymmetric structure to be obtained with less, or no, solvent in the precipitation bath, which simplifies the production process.

To aid in adjusting the pore structure of the asymmetric microporous beads of the present invention, the polymer solution optionally may contain a liquid nonsolvent for the polymer, in sufficient quantities (0 to 60 wt %) that the polymer does not begin to precipitate, but remains completely dissolved prior to spraying. Such nonsolvent can increase the porosity of the interior of the bead as well as facilitate the characteristic continuous gradation of pore sizes from the interior to the surface. Examples of suitable nonsolvents include water, alcohols such as ethanol, n-propanol and 2-methoxyethanol, glycerol, and acetone for the preferred case of an organic solvent and an aqueous precipitation bath.

Preferably, droplets of polymer solution are formed by spraying the solution through a nozzle into a precipitation bath. The nozzle may be a single-fluid nozzle of an airless design, or a two-fluid nozzle with either air stripping or external mixing. Air stripping nozzles are generally preferred, since they facilitate good control of the bead size distribution. Beads thus produced are generally from 5 microns to 2 mm in diameter, depending on air and solution pressure, temperature, viscosity, and external air flow. The precipitation bath contains a liquid that is miscible with the solvent and that is a nonsolvent for the polymer. It may also include one or more surfactants that assist in producing beads of a spherical shape and having a more uniform pore structure. The precipitation bath may also contain a solvent for the polymer, so long as it is present in sufficient quantity, typically 5 to 50 wt %, that the polymer still precipitates in the bath. As mentioned above, inclusion of such a solvent slows precipitation of the beads, resulting in reproducible continuously-gradated pores from large pores in the interior to small ones at the surface.

An alternative method, especially useful for producing large beads, is to allow the polymer solution to simply drip out of the nozzle into the precipitation bath. Depending on the nozzle size, the solution surface tension and the viscosity, beads of from 2 to 5 mm in diameter can be produced in this manner. Another method of production is to allow the polymer solution to drip out of the nozzle, and impinge an air stream onto the droplets at the nozzle or as they fall into the precipitation bath, creating beads from about 40 microns to about 2 mm in diameter.

Still another method of preparing beads of the present invention is to spray droplets of a polymer solution containing at least one nonsolvent liquid into an air chamber without the use of a liquid precipitation bath. In this case, the solvent must be sufficiently volatile that it evaporates from the droplet in the air chamber, causing the polymer droplet to precipitate mid-air. The polymer precipitates around microdroplets of the nonsolvent, resulting in a microporous structure, as in the case when a precipitation bath is used. The rapid evaporation of the solvent at the surface of the droplet results in very small pores at the surface, with progressively larger pores toward the core. The nonsolvent must be less volatile than the solvent, but should be miscible with the polymer solution in the quantities used, and may be volatile, so that it can be evaporated from the beads following production. Alternatively, the nonsolvent may be removed from the beads by leaching into another miscible, volatile liquid that is then removed by evaporation. A different alternative, especially useful when the active ingredient has the appropriate nonsolvent properties mentioned above, is to use the active ingredient, or a solution of the active ingredient, as the nonsolvent. In this case, essentially all of the active ingredient remains in the beads following production, eliminating the need for a separate loading step, but without the attendant waste of prior art methods. Water, alcohols, and glycerol are examples of nonsolvents useful for polymers dissolved in organic solvents.

Yet another method consists of feeding the polymer solution to the top surface of a spinning disk. Centripetal acceleration forces the solution to the outer rim of the disk, where droplets of solution separate from the disk and are propelled into an air chamber. The droplets may fall into a precipitation bath or may dry in the air chamber without a precipitation bath, as described above.

The beads produced by the above methods have total porosities of between 50 and 90%, although lower porosities are also possible. Even very small beads (less than 100 microns in diameter) have porosities in this range. The microporous structure of the beads is of an asymmetric nature, as can be seen in FIG. 1. Very small (typically less than 0.1 micron diameter), or no, pores are present in the thin skin at the surface of the bead, and these pores increase in size in a continuous manner toward the interior, where they may be as large as about 25% of the diameter of the bead. As mentioned, this characteristic continuous gradation in pore size is achieved through a combination of rapid initial precipitation of the polymer at the droplet or evolving bead surface, followed by relatively slow solvent exchange and polymer precipitation in the interior. This combination of initially rapid and subsequently slow precipitation steps is achieved through control of the temperature and composition of the precipitation bath, as well as by the composition and viscosity of the polymer solution, all as discussed in greater detail above. Generally, cool temperatures are preferred (less than 25° C.), to effect rapid surface precipitation and slow solvent exchange.

The characteristic continuous gradation in pore size from very small at the surface to very large at the core allows the active ingredient to continuously migrate from the interior to the surface pores by capillarity, thus maintaining constant contact with the surface. The rate of release of active ingredient from the beads can only be constant if there is a constant concentration of active ingredient (either pure active ingredient or a saturated solution) within the bead and a constant active ingredient-releasing surface area of release. Release rates of prior art porous beads are typically not constant, since the portion of the surface area that releases active ingredient gradually decreases with time due to depletion of the active ingredient from the surface, leaving active ingredient only in the interior pores. The constant rate of release from the beads of the present invention is achieved in part due to the maintenance of a constant active ingredient-releasing surface area by continuous migration of the active ingredient toward the surface. The constant rate of release is also due to the presence of active ingredient at unit thermodynamic activity within the bead, which maintains a constant driving force for diffusion out of the bead. Different release rates are achieved by using polymers with different permeabilities, or by varying the bead size and surface porosity.

Active ingredients to be loaded into the beads may be liquid, solid, or solid in solution. In liquid or solution form, the active ingredient may be loaded by submerging dry, empty beads in the liquid consisting of or containing the active ingredient, and then either drawing a vacuum on the solution to remove the air from the beads allowing the liquid to enter, or pressurizing the solution to force it into the beads. The beads can also be loaded by simply soaking them in the active ingredient for several hours or days, but vacuum or pressure loading is preferred. Typically, drawing a vacuum down to about 1 to 20 mmHg for 10 minutes to two hours is sufficient to load the beads. Alternately, drawing and releasing the vacuum during that time often increases the loading and/or the rate of loading. The degree of vacuum and the time to load are both independent on the active ingredient and the polymer; low-molecular-weight active ingredients that exhibit a low interfacial surface tension with the polymer load most rapidly. Conversely, active ingredients with high molecular weights and/or high interfacial surface tension with the polymer may require greater vacuum for a longer time. In the typical case of pressurized loading, pressurizing the liquid to 20–200 psi for 20 minutes to four hours is sufficient to fully load the beads.

Solid active ingredients may be loaded into the beads either as the beads are being made, or after they are made. In the former case, particles of the active ingredient may be dispersed in a solution of polymer and solvent, which is then formed into beads as described above. In the case of loading solid active ingredients into the beads after their preparation, the solid active ingredient may be dissolved in a solvent compatible with the polymeric bead to form a solution, which is then loaded into the beads in the same way as liquid active ingredients. If high loadings are desired, the solvent may be evaporated or extracted from the beads after loading, and then the loading process repeated with a saturated solution of active ingredient in solvent. By using a saturated solution, none of the active ingredient present in the beads after the first loading is redissolved, and additional active ingredient may be loaded into the beads with each repetition of the loading process.

Active ingredients, the release of which could be improved by loading into the asymmetric microporous beads of the present invention, include insect porous beads of the present invention, include insect pheromones, insect attractants, insecticides, insect growth regulators, fungicides, herbicides, fertilizers, plant growth regulators, micronutrients, pharmaceuticals, antibacterials, deodorants, fragrances cosmetics, flavors, food additives, foods such as sugars or amino acids, oils, lubricating agents, chemical reactants, catalysts, antiscaling compounds, corrosion inhibitors, water, and the like.

Examples of insect pheromones include gossyplure, grandlure, disparlure, muscalure, japonilure, trimedlure, codlemone, virelure, and periplanonen B.

Examples of insecticides include naled, diazinon, propoxur, fenoxycarb, chlorpyrifos, malathion, methyl parathion, carbaryl, methomyl, permethrin, fenvalerate, cypermethrin, aldicarb, acephate, carboiuran, and dichlorvos.

Examples of herbicides include alachlor, butylate, propham, chlorpropham, EPTC, lactofen, tebulate, triallate, and vernolate.

Combinations of active ingredients can also be loaded into the beads. For example, beads loaded with an insecticide combined with an insect pheromone may prove especially useful.

In addition to active ingredients, other ingredients that protect the active ingredient or impart other useful characteristics may be loaded into the beads. Such other ingredients include pigments, dyes, antioxidants, antiozonants, ultraviolet-light inhibitors, bacteriostatic agents, and the like. Asymmetric microporous beads loaded with liquid active ingredients often have specific gravities less than 1 g/CM$^3$, especially if the loading is high. The specific gravity can be increased to enable stable suspensions in water, for example, by using a polymer with a high density, by lowering the porosity (and therefore the loading), or by adding a high-density material to the beads. Metals or other high-density particles such as inorganic solids may also be loaded into the beads to increase their density.

After the beads are loaded with active ingredient, they also may be coated with a separate nonporous polymeric coating to further retard release of active ingredient or to protect the active ingredient during storage or use. Such coatings may be applied using any of a variety of conventional coating techniques, such as spray drying, spray coating, fluidized-bed coating, or pan coating.

The rate of release of active ingredients from asymmetric microporous beads is controlled largely by the rate of diffusion through the relatively dense "skin' at the surface of each bead. Increasing the thickness of this skin or reducing its porosity generally lowers the permeability of an active ingredient through the skin, and so lowers its release rate. This can be done either by heating the surface of the beads to melt the polymer at the surface (but not in the interior of the bead), or by contacting the bead surface with solvent that partially dissolves the polymer at the surface (but not in the interior). These treatments are preferably conducted in a fluidized bed or other chamber so as to minimize agglomeration.

EXAMPLE 1

Asymmetric microporous beads made of polysulfone were prepared by first dissolving polysulfone in dimethylformamide at a concentration of 120 g/L, which yielded a polymer solution having a viscosity of about 500 cps at 25° C. This polymer solution was pressurized to approximately 30 psi and forced through an 18-gauge needle to drip into a stirred precipitation bath containing 0.5 wt % surfactant in water at 20° C. Beads approximately 2 to 3 mm in diameter were formed with substantially the structure shown in FIG. 1. The beads were then dried and loaded with the insect pheromone gossyplure by submerging the beads in a flask of gossyplure and drawing a vacuum. The vacuum was alternately drawn and released three times over a period of about 30 minutes, yielding an 86 wt % gossyplure loading of the beads.

EXAMPLE 2

Asymmetric microporous beads made of polysulfone were prepared as in Example 1, with the exception that the polysulfone concentration was 160 g/L, and the viscosity was about 1200 cps. These beads were also approximately 2 to 3 mm in diameter. The beads were dried and then loaded to 81 wt % gossyplure as in Example 1, with the exception that the vacuum was alternately drawn and released 10 times over three hours.

EXAMPLE 3

The polymer solution of Example 1 was sprayed out of a 23-gauge needle approximately 2 to 3 feet through the air into substantially the same precipitation bath as in Example 1. The beads formed were approximately 0.6–1.0 mm in diameter and had an internal porous structure substantially as shown in FIG. 1. The beads were dried and loaded to 88 wt % gossyplure as in Example 1.

EXAMPLE 4

Asymmetric microporous beads made of polysulfone were prepared and loaded to 74 wt % gossyplure as in Example 3 with the exception that the polysulfone concentration was 160 g/L and the viscosity of the polymer solution was about 1200 cps. The beads formed were of the same size and structure as those of Example 3.

EXAMPLE 5

Asymmetric microporous beads made of polyvinylidenefluoride (PVDF) were prepared by first dissolving PVDF in dimethylformamide at a concentration of 12.5 wt % which yielded a polymer solution having a viscosity of about 1000 cps at 25° C. This solution was then pressurized to approximately 30 psi and dripped from a 23-gauge needle into a stirred precipitation bath consisting of 10 wt % dimethylformamide and 0.1 wt % surfactant in water at 20° C. Beads approximately 2 to 3 mm in diameter were formed with substantially the same structure shown in FIG. 1.

EXAMPLE 6

Asymmetric microporous PVDF beads having the same structure as those of Example 5 were prepared as in that Example, with the exception that the polymer solution also contained 1 wt % Waxoline black (ICI Chemicals) as a color additive, 0.5 wt % UOP688 (UOP, Inc.) as an antioxidant, and 0.25 wt % Tinuvin 328 (Ciba Geigy Corp.) as an ultraviolet light absorber. The resulting beads were dried and then loaded to 60 wt % gossyplure by submerging the beads in gossyplure and pressurizing the solution at 100 psi for one hour.

EXAMPLE 7

Asymmetric microporous beads made of polyvinylchloride (PVC) were prepared by first dissolving PVC in heated dimethylformamide at a concentration of 75 g/L, which yielded a polymer solution having a viscosity of 900 cps at 45° C. This solution was then sprayed out of a nozzle into a stirred precipitation bath containing 15 wt % dimethylformamide and 0.1 wt % surfactant in water at 19° C. The resultant beads were approximately 900 microns in diameter and had the structure shown in FIG. 1. The beads were then dried and pressure-loaded to 81 wt % gossyplure as in Example 6.

EXAMPLE 8

Asymmetric microporous beads approximately 1.0 mm in diameter and having substantially the same structure shown in FIG. 1 were prepared as in Example 3. The beads were then dried and pressure-loaded to 80 wt % with the organophosphate insecticide diazinon (dimpylate) as in Example 6.

EXAMPLE 9

Asymmetric microporous beads approximately 1 mm in diameter and having substantially the same structure shown in FIG. 1 were prepared as in Example 3. The beads were then dried and pressure-loaded as in Example 6 to 78 wt % with the pheromone of the insect Heliothis armigera—a mixture of 95 wt % cis-11-hexadecenal and 5 wt % cis-9hexadecenal.

EXAMPLE 10

Asymmetric microporous beads made of polyurethane were prepared by first dissolving polyurethane (Tuftane 310 polyester-based polyurethane, Lord Corp.) in dimethylformamide at a concentration of 20 wt % t which yielded a polymer solution having a viscosity of about 1200 cps at 25° C. This solution was then dripped into a precipitation bath consisting of a solution of 0.1 wt % surfactant in water at 20° C. The beads formed were approximately 2 to 3 mm in diameter and had substantially the structure shown in FIG. 1. The beads were then pressure-loaded to 82 wt % with pine oil as in Example 6.

EXAMPLE 11

Asymmetric microporous cellulose acetate beads having the same size and structure as those of Example 10 were prepared in the same manner as in that Example, except that the polymer solution was made by dissolving cellulose acetate (CA398-10, Eastman Chemicals) in a mixture of 10 wt % dichloromethane and 90 wt % dimethylformamide at a concentration of 10 wt %, to yield a polymer solution having a viscosity of about 800 cps at 25° C. The beads were then pressure-loaded to 79 wt % with pine oil as in Example 6.

EXAMPLE 12

Asymmetric microporous PVC beads were prepared by first dissolving PVC in heated dimethylformamide at a concentration of 10 wt %, which yielded a polymer solution having a viscosity of about 1500 cps at 40° C. This solution was then pressurized to 40 psi and sprayed out of a 50-micron diameter nozzle into a precipitation bath containing 0.1 wt % surfactant in water at 20° C. The beads formed were approximately 200 to 400 microns in diameter and had the same structure shown in FIG. 1. The beads were then pressure-loaded to 85 wt % with pine oil as in Example 6.

EXAMPLE 13

Asymmetric microporous polysulfone beads from Example 3 were loaded with the solid insecticide chlorpyrifos by immersing the beads in a solution of 61.5 wt % chlorpyrifos in xylene. A vacuum was alternately imposed and released for approximately 25 minutes. The beads were then removed from the solution and were dried overnight. The content of chlorpyrifos in the beads after drying was determined to be 55 wt %.

EXAMPLE 14

Asymmetric microporous beads were prepared as in Example 1 from a solution of 16 wt % polysulfone in dimethylformamide that also contained 1.8 wt % zinc metal powder dispersed in the solution to increase their density.

EXAMPLE 15

The PVDF beads from Example 5 were placed on an aluminum foil tray above a butane burner and kept there until the beads began to turn translucent and shrink slightly, evidencing a reduced porosity. The beads were then removed from the heat source, were cooled, and were loaded with an insect pheromone.

EXAMPLE 16

Figure 2:
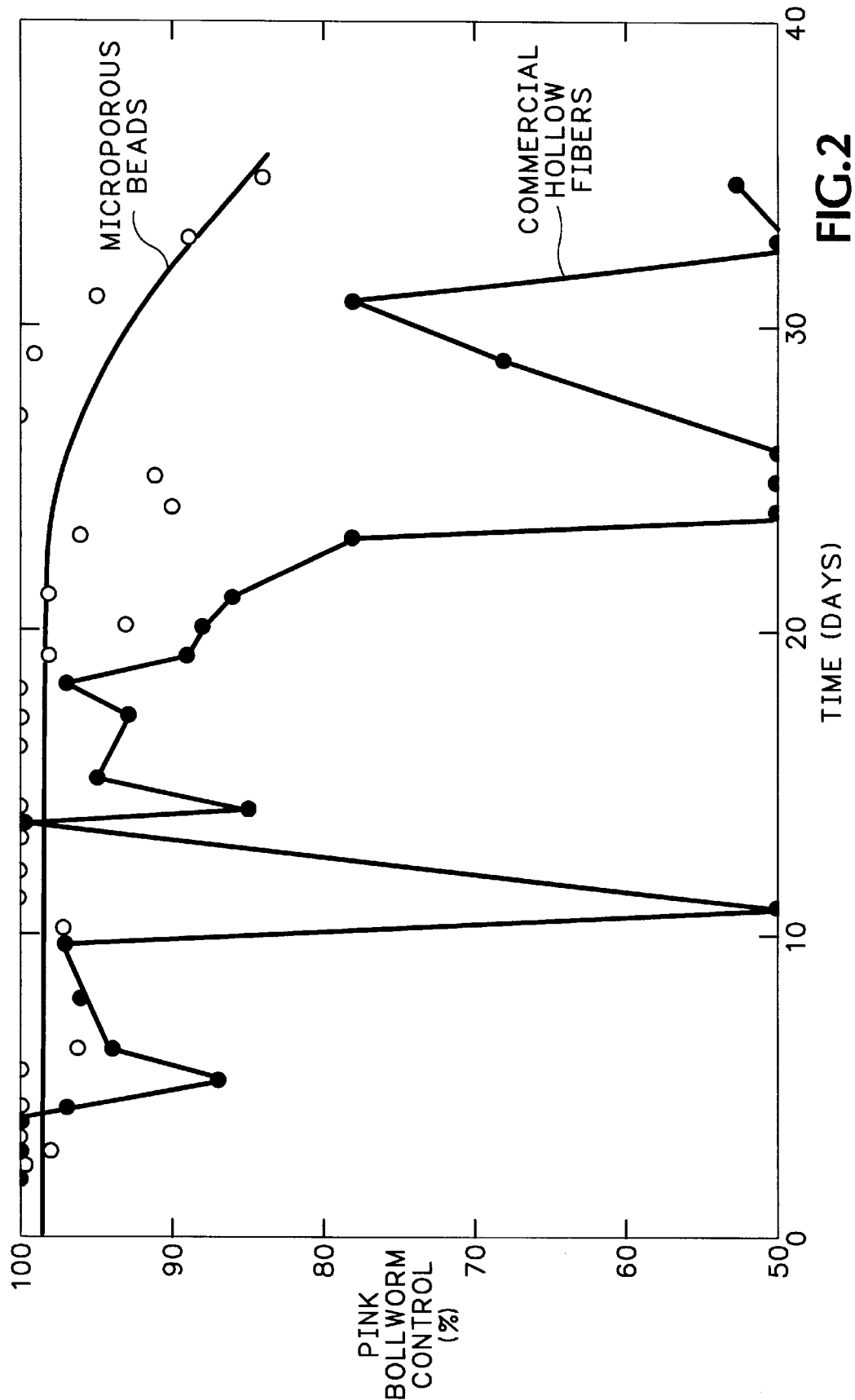
FIG. 2 is a graph showing the results of field tests of the beads of the present invention loaded with an insect pheromone.

The gossyplure-loaded beads of Example 3 were suspended in a mixture of 5 wt % acrylic latex emulsion (available as Gelva RA1990 from Monsanto Corp.) and 0.1 wt % surfactant in water to make up 30 gal. of the suspension and applied to 10 acres of cotton plants in Arizona by aerial spraying at an application rate of 3 gal/acre. Examination of the so-sprayed beads showed them to be intact, with no indication of any rupturing. The efficacy of the beads in controlling pink bollworm in cotton is shown in FIG. 2, measured by reduction in trap catch of pink boll-worm moths in the field. As shown, the beads provided 90% reduced trap catch for over 30 days, compared with less than 20 days for a commercial controlled-release product comprising gossyplure-loaded hollow fibers ("No-Mate" by Albany International of Needham Heights, Mass.).

EXAMPLE 17

Figure 3:
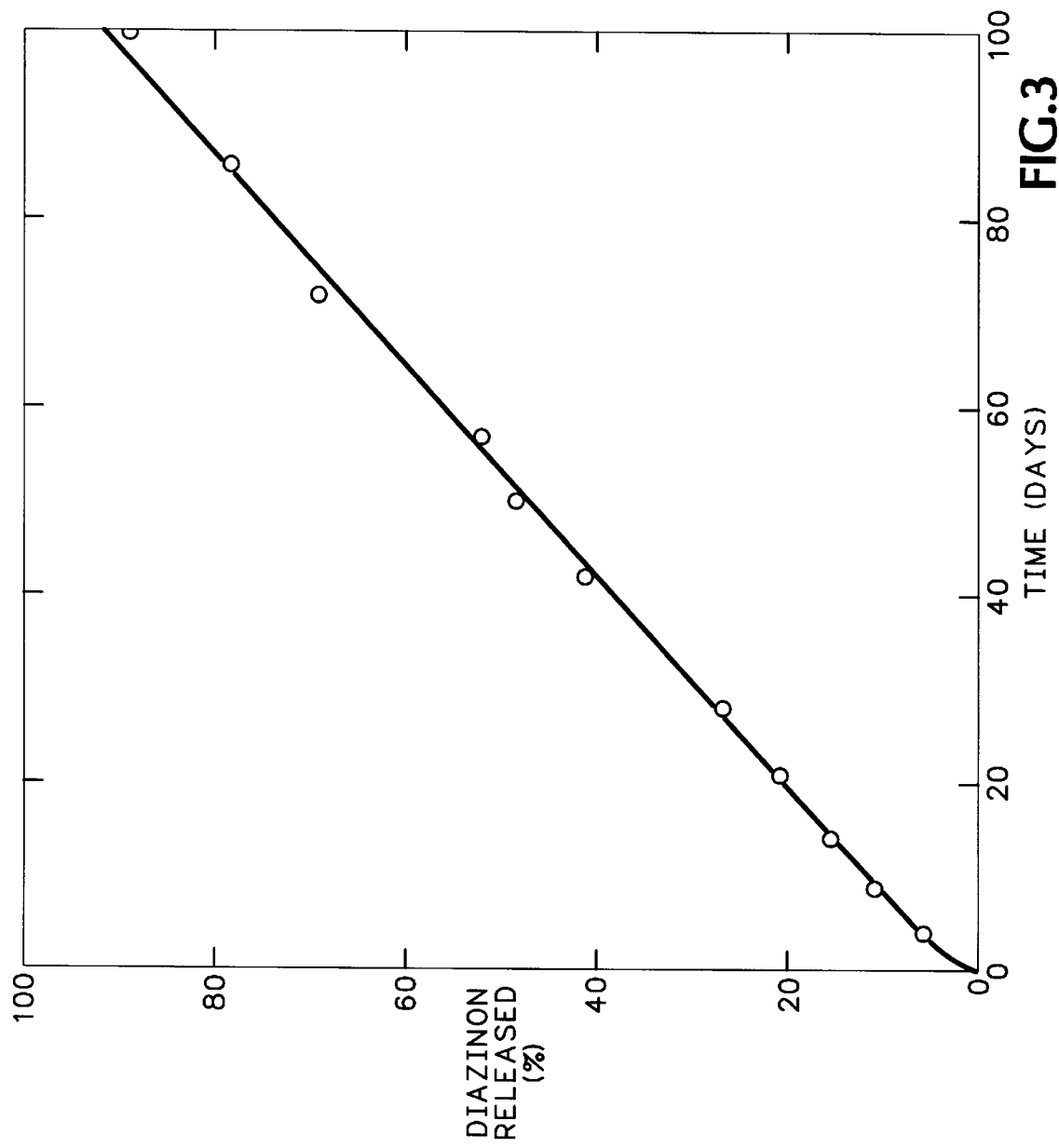
FIGS. 3 and 4 are graphs showing rates of release over time of various active ingredients by the beads of the present invention.

The diazinon-loaded beads of Example 8 were stored for several months in a controlled-temperature chamber at 25° C. The beads were weighed periodically to determine the quantity of diazinon that had been released. FIG. 3 shows the cumulative quantity of the insecticide released from the beads over a period of 100 days. The release rate was constant over the entire measured duration of release. The projected duration of release was about four months.

EXAMPLE 18

Figure 4:
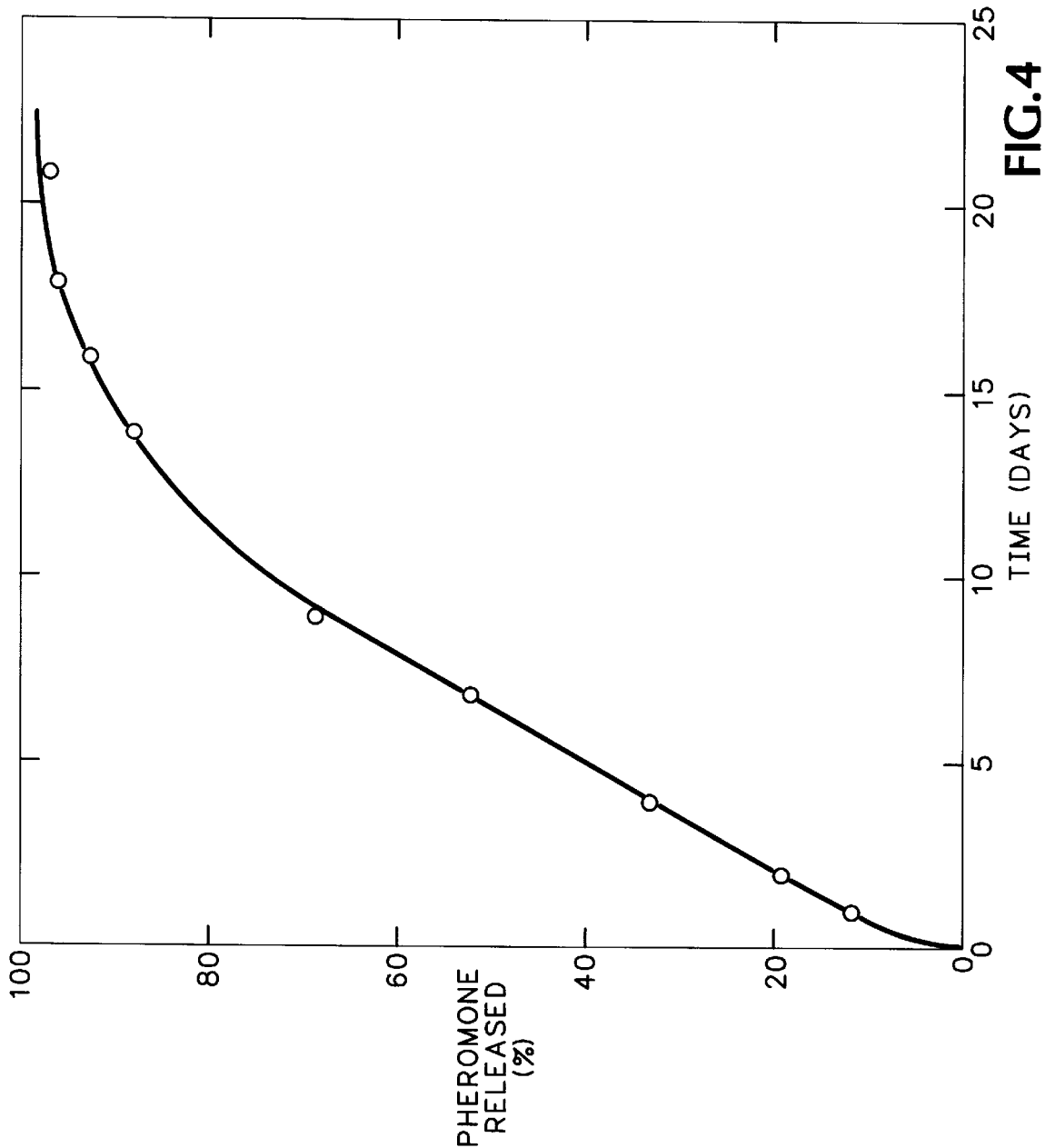

The pheromone-loaded beads of Example 9 were stored and their rate of release of the pheromone was determined as in Example 17. As shown in FIG. 4, the rate of release was constant until about 80% of the pheromone had been released, and the duration of release was about 20 days.

EXAMPLE 19

Asymmetric microporous beads containing a solid active ingredient (the drug trimazosin) were prepared as follows. Bead cores consisting of 30 wt % trimazosin and 70 wt % microcrystalline cellulose and approximately 1 mm in diameter were dispersed in a solution of 15 wt % cellulose acetate, 33 wt % ethanol, and 52 wt % acetone. The resulting suspension was dripped from a pipette into a water bath at room temperature to form beads 2–3 mm in diameter with an asymmetric microporous structure having one or more bead cores in the center of each bead. The beads were collected and dried, and the release of trimazosin from the beads into water was then determined. The trimazosin was released at a constant rate for a total of 6 hours, at which time all of the drug had been released.

EXAMPLE 20

The gossyplure-loaded beads of Example 7 were suspended in a mixture of 2.0 wt % sticker (Raincoat) and 0.2 wt % surfactant (Activate Plus, Riverside/Terra Corp., Sioux City, Iowa) in water. The concentration of beads was 160 g of loaded beads in 60 gal water. This mixture was agitated in a pre-mix tank for 3 min and then pumped into the hopper of an Ag-Cat airplane. The screens were removed from the spray boom. The mixture was applied to 10- to 15-acre plots of cotton near Queen Creek, Ariz. from the airplane at a rate of 3 gal/acre. The beads were pumped and sprayed without any rupturing and with no clogging of the boom, and the formulation successfully controlled pink bollworm for more than two weeks.

EXAMPLE 21

Gossyplure-loaded beads were prepared as in Example 7 with the exception that the bead diameter was approximately 100 $\mu$m and the gossyplure loading was 85 wt %. The beads were suspended in a mixture of 1.6 wt % sticker (Nu-Film P) and 0.2 wt % surfactant (Kinetic) in water. The concentration of beads was 120 g of loaded beads in 45 gal water. This mixture was agitated in a pre-mix tank for 3 min and then pumped into the hopper of an Ag-Cat airplane. The spray boom was fitted with 50-mesh screens. The mixture was applied to 10- to 15-acre plots of cotton near Queen Creek, Ariz. from the airplane at a rate of 3 gal/acre. The beads were pumped and sprayed without any rupturing and with no clogging of the boom, and the formulation successfully controlled pink bollworm for more than 10 days.

EXAMPLE 22

Gossyplure-loaded beads were prepared as in Example 21. The beads were suspended in a mixture of 0.4 wt % sticker (Raincoat,) and 0.2 wt % surfactant (Agri-Dex, Helena Chemical Co., Memphis, Tenn.) in water. The concentration of beads was 120 g of loaded beads in 210 gal water. The mixture was added to the hopper of a John Deere Hi-Cycle tractor with continuous agitation for spray application from the tractor's spray boom. The spray boom contained 37 D-2 nozzles fitted with 100-mesh screens on the main boom. The mixture was applied to 10- to 15-acre plots of cotton near Coolidge, Ariz. The beads were pumped and sprayed without any rupturing and with no clogging of the boom, and the formulation successfully controlled pink bollworm for more than 10 days.

The terms and expressions which have been employed in the foregoing specification are used therein as terms of description and not of limitation, and there is no intention/in the use of such terms and expressions, of excluding equivalents of the features shown and described or portions thereof, it being recognized that the scope of the invention is defined and limited only by the claims which follow.

We claim:

1. A method of controlling agricultural pests comprising:
   (a) providing polymeric microporous beads with a diameter of from 5 $\mu$m to 5 mm having no rate-controlling membrane wall applied to their surface and having an anisotropic pore structure of large pores in the interior and small pores near the surface, the gradation of pore sizes between the interior and the surface being continuous;
   (b) preparing loaded beads by loading said beads with at least one active ingredient selected from the group consisting of a pheromone, an insect growth regulator and an insecticide;
   (c) preparing an emulsion by suspending said loaded beads in an aqueous emulsion; and
   (d) applying said emulsion to vegetation.

2. The method of claim 1, including loading said beads with at least one agent selected from the group consisting of an antioxidant and a UV light inhibitor.

3. The method of claim 1 wherein said active ingredient comprises the pheromone gossyplure and said vegetation comprises cotton plants.

4. The method of claim 1 wherein step (d) is conducted by spraying.

5. A device for the controlled release of active ingredient consisting essentially of a polymeric microporous bead with a diameter of from 5 $\mu$m to 5 mm having no rate-controlling membrane wall applied to its surface and having an anisotropic pore structure of large pores in the interior and small pores near the surface, the gradation of pore sizes between the interior and the surface being continuous, the pores of said bead having been loaded with active ingredient following fabrication of said bead, wherein said active ingredient is in a form selected from liquid active ingredient and solid active ingredient in solution, and wherein said active ingredient is selected from a pheromone, an insect growth regulator, a fragrance, a flavor, a food, an insecticide, a fungicide, a herbicide, a plant growth regulator, a fertilizer, a micronutrient and a pharmaceutical, and combinations thereof.

6. The device of claim 5 wherein said polymeric microporous bead is made from a polymer selected from polycarbonates, polysulfones, polyethersulfones, polyamides, polyurethanes, acrylic resins, polyvinylchlorides, polyvinylfluoride, polyacrylonitrile, polystyrene, polyolefins, polyvinylidenechloride, polyvinylidenefluoride, polyethyleneterephthalate, polybutyleneterephthalate, cellulosic esters, polyimides, polyacetals, polyvinylacetate, polyphenyleneoxide, polyetherimides, ethylene-vinylalcohols, and derivatives and copolymers thereof.

7. The device of claim 5 wherein said active ingredient is a pheromone selected from gossyplure, grandlure, disparlure, muscalure, japonilure, trimedlure, codlemone, virelure, and periplanone B.

8. The device of claim 5 wherein said active ingredient is an insecticide selected from naled, diazinon, propoxur, fenoxycarb, chlorpyrifos, malathion, methyl parathion, carbaryl, methomyl, permethrin, fenvalerate, cypermethrin, aldicarb, acephate, carbofuran, and dichlorvos.

9. The device of claim 5 wherein said active ingredient is a herbicide selected from alachlor, butylate, propham, chlorpropham, EPTC, lactofen, tebulate, triallate, and vernolate.

10. The device of claim 5 containing from 50 to 90 wt % active ingredient.

11. The device of claim 5 wherein the surface of said polymeric microporous bead is treated by a method selected from heating and contact with a solvent.

12. The device of claim 5 additionally containing one or more additives selected from antioxidants, pigments, dyes, ultraviolet light absorbents, and inorganic solids.

* * * * *

UNITED STATES PATENT AND TRADEMARK OFFICE
CERTIFICATE OF CORRECTION

PATENT NO. : 5,888,930  
DATED : March 30, 1999  
INVENTOR(S) : Smith, Holmes, Brooke Page 1 of 1

It is certified that error appears in the above-identified patent and that said Letters Patent is hereby corrected as shown below:

Column 5,  
Line 53, delete "•" after "skin at the"

Column 7,  
Line 48, change "skin' to read -- "skin"

Column 9,  
Lines 25-26, change "cis-9hexadecenal" to read -- cis-9-hexadecenal --  
Line 32, delete [t] after "20 wt%"

Signed and Sealed this

Eighth Day of January, 2002

Attest:

*Attesting Officer*

JAMES E. ROGAN  
*Director of the United States Patent and Trademark Office*